United States Patent [19]

Ninomiya et al.

[11] Patent Number: 5,470,985

[45] Date of Patent: Nov. 28, 1995

[54] METAL COMPLEX COMPOUND

[75] Inventors: Hidetaka Ninomiya; Yuko Nagasawa; Kazuo Asano, all of Hino, Japan

[73] Assignee: Konica Corporation, Japan

[21] Appl. No.: 278,172

[22] Filed: Jul. 21, 1994

[30] Foreign Application Priority Data

Jul. 27, 1993 [JP] Japan .................................. 5-185207

[51] Int. Cl.⁶ .................................. C07D 231/10
[52] U.S. Cl. .................. 548/312.4; 548/202; 548/203; 548/205; 548/235; 548/316.4; 548/317.1; 548/326.5; 548/331.5; 548/335.1; 548/342.1; 548/343.5; 548/346.1; 546/278; 544/124
[58] Field of Search .................. 548/312.4, 316.4, 548/317.1, 326.5, 331.5, 333.1, 335.1, 342.1, 343.5, 346.1, 202, 203, 205, 235; 546/278; 544/124

[56] References Cited

U.S. PATENT DOCUMENTS 3,432,300   3/1969   Lestina et al. .................... 96/74
4,050,938   9/1977   Smith, Jr. et al. ................ 96/84

*Primary Examiner*—Joseph K. McKane
*Attorney, Agent, or Firm*—Jordan B. Bierman; Bierman and Muserlian

[57] ABSTRACT

A metal complex compound is disclosed. The compound is represented by the following formula I or II:

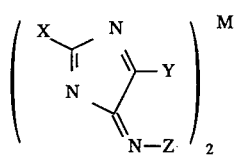

(I)

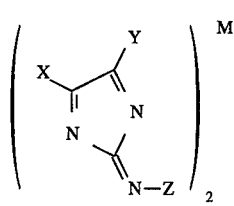

(II)

15 Claims, No Drawings

METAL COMPLEX COMPOUND

FIELD OF THE INVENTION

This invention relates to a novel metal complex compound having excellent characteristics to serve as a dye, which is useful to an optical recording medium applied with the same compound to serve as a light absorption material.

BACKGROUND OF THE INVENTION

A dye having been well-known as a dyestuff or a pigment has widely been utilized in various applications such as a dyestuff for textile, a colorant for resin or paint, an image-forming material for photography, graphic arts, copier and printer use, and a photoabsorbing material for color filter use.

Common problems of these dyes to be solved include, for example, optimization of absorption wavelength and form of spectral absorption curve, an improvement of a molar absorption coefficient, and a preservability improvement including, typically, light stability or thermal stability.

For forming a full-color or three primary colors, three kinds of dyes, yellow, magenta and cyan, are required. Particularly, a cyan dye having an excellent absorption characteristic and a preservation stability has been needed.

On the other hand, with the rapid increase in information volume, a large volume optical recording medium has received much attention. In an organic optical recording medium capable of simple and high density information-recording with a relatively inexpensive semi-conductor laser, a relatively long wavelength-absorbing dye capable of absorbing rays of light from a red region to a near infrared region is used. Heretofore, among a variety of dyes, a cyanine dye excellent in both absorption and reflection characteristics has been utilized for this purpose. However, the cyanine dyes have had a shortcoming that in information data is lost in storage or record ability declines because stability such as light stability of the dye was low.

For solving the above-mentioned problems, for example, U.S. Pat. Nos. 3,432,300 and 4,050,938 and Japanese Patent Publication Open to Public Inspection (hereinafter referred to as JP OPI Publication) Nos. 60-118748/1985, 63-199248/1988 and 2-300288/1990 disclose each a light stabilizer or a light stabilizing process. However, there have not yet accomplished to obtain any satisfactory preservation stability. On the other hand, JP OPI Publication Nos. 64-44786/1989, 2-76884/1990 and 5-17701/1993 each disclose a metal chelating dye excellent in preservation stability. However, the metal chelating dyes have not been able to be applied as an optical recording medium, because their absorption wavelengths have been too long to be used.

SUMMARY OF THE INVENTION

The object of the invention is to provide dyes, particularly a cyan dye, with a very high molar absorption coefficient and excellent in light stability.

Another object of the invention is to provide an optical recording medium of which the optical recording characteristics and preservation stability can be made excellent by application of a dye having an absorption suitable for a semi-conductor laser used for an optical recording apparatus, high in molar absorption coefficient and excellent in light stability.

The metal complex compound of the invention is represented by formula I or formula II;

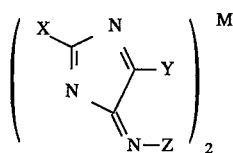

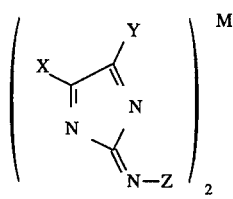

where X and Y are each a hydrogen atom or a group of non-metal atoms, provided that at least one of X and Y is an aryl group having a substituent selected from a hydroxyl group, a mercapto group, an acyl substituted amino group having an electron withdrawing group as a substituent, an alkylsulfonamido group, an arylsulfonamido group, an alkoxy group, an alkylthio group, an arylthio group and an alkylamino group, or a heterocyclic group; Z is an aryl group having a hydroxyl group, an amino group, an alkyl amino group, an alkoxyl group, an anilino group, an acylamino group or an alkylsulfonamido group as a substituent at the para-position thereof; and M is $Ni^{2+}$ ion or its salt, $Cu^{2+}$ ion or its salt, $Co^{2+}$ ion or its salt, $Zn^{2+}$ ion or its salt, $Fe^{2+}$ ion or its salt, $Pd^{2+}$ ion or its salt, or $Pt^{2+}$ ion or its salt.

DETAILED DESCRIPTION OF THE INVENTION

The metal complex compounds of the invention will further be detailed hereunder.

In the foregoing formula I or II, when X and Y each represent a group consisting of non-metal atoms, the examples, when this is the case, include a halogen atom, a cyano group, a hydroxyl group, an amino group, an alkyl group, an aralkyl group, a cycloalkyl group, an alkenyl group, an alkoxy group, a sulfonamido group, an anilino group, a mercapto group, an acylamino group, a ureido group, an alkoxycarbonyl group, a sulfonylamino group, a carbamoyl group, a sulfamoyl group, a sulfo group, a carboxy group, an alkoxycarbonylamino group, an aryl group and a heterocyclic group. When X and Y each represent a substituent capable of bonding to M, the examples thereof include an aryl group substituted with a hydroxyl group, a mercapto group, an acylamino group substituted with an electron withdrawing group, an alkylsulfonamido group, an arylsulfonamido group, an alkoxy group, an alkylthio group, or an arylthio group, an alkylamino group and a heterocyclic group.

In order that a substituent capable of bonding to the above-mentioned M forms a bond to M, it is required to have lone paired electrons or an anionic dissociation group in a position adjacent to the imidazole ring.

It may be considered that a group such as a hydroxyl group, a mercapto group, an acylamino group, substituted with an electron withdrawing group such as an alkylsulfonamido group, and an arylsulfonamido group, may be able to form a bond, as an anionic dissociation group.

The acylamino groups each substituted with an electron withdrawing group include, for example, a trichloroacetamido group, a heptafluoropropylamido group and a 4-nitrobenzamido group. The above-mentioned electron withdrawing groups herein mean those showing a positive value in terms of a Hammett's σ value such as, a halogen atom, a cyano group, a nitro group and an alkylsulfonamido group.

Examples of an alkylsulfonamido group, which is capable of bonding with M, include a methylsulfonamido group, an ethylsulfonamido group and an octylsulfonamido group, a 2,2,2-trifluoroethylfonamido and a 2,2,3,3-tetrafluoropropylsulfonamido. Examples of an arylsulfonamido group include a phenylsulfonamido group, a tosylsulfonamido group and a naphthylsulfonamido group. Examples of an alkoxy group include a methoxy group, an ethoxy group, a propyloxy group and 2-ethylhexyloxy group. Examples of an alkylthio group include a methylthio group, an ethylthio group, a propylthio group and an octylthio group. Examples in the case of an arylthio group include a phenylthio group and naphthylthio group. Examples of an alkylamino group include a methylamino group, an ethylamino group, an N,N-dimethylamino group and an N-ethyl-N-hexylamino group.

Examples of an aryl group having a substituent capable of bonding to the foregoing M include Chose having such a structure that a phenyl group, a naphthyl group or an anthranyl group is substituted with any one of the above-given a hydroxyl group, a mercapto group, an acylamino group, substituted with an electron withdrawing group, an alkylsulfonamido group, an arylsulfonamido group, an alkoxy group, an alkylthio group, an arylthio group, an alkyl amino group. Concrete examples of the aryl group include a 2-tosylsulfonamidophenyl group, a 2-methyl sulfonamidophenyl group, a 5-ethoxy-2-tosylsulfonamidophenyl group, a 5-isopropylamido-2-tosylsulfonamidophenyl group, a 2-hydroxyphenyl group, a 2-(2-benzimidazolyl)phenyl group, a 2-heptafluoropropylamido group and a 2-tosylsulfonamidonaphthyl group. Examples of a heterocyclic group include a pyridyl group, a piperazyl group, a pyrimidyl group, a thiazolyl group, a benzthiazolyl group, an oxazolyl group, an imidazolyl group and a benzimidazolyl group. Among them, a 1-pyrazolyl group, a 2-pyridyl group, a 2-benzthiazolyl group, a 2-imidazolyl group, a 2-benzimidazolyl group and a 2-hydroxy-3-pyridyl group are preferred.

Examples of group represented by Z include a 4-hydroxyphenyl group, a 3,5-dichloro-4-hydroxyphenyl group, a 4-aminophenyl group, a 4-(N-methylamino)phenyl group, a 4-(N-ethylamino)phenyl group, a 4-(N-hexylamino)phenyl group, a 4-(N-dodecylamino)phenyl group, a 4-(N,N-dimethylamino)phenyl group, a 4-(N,N-diethylamino)phenyl group, a 4-(N,N-dihexylamino)phenyl group, a 4-(N-ethyl-N-methylsulfonamido)phenyl group, a 4-(N,N-diethylamino-3-methyl)phenyl group, a 4-(N,N-dihexylamino)-2-methylphenyl group, a 4-(N-ethyl-N-methanesulfonamido)-2-methylphenyl group, a 4-(N-ethyl-N-hydroxyethyl)-2-methylphenyl group, a 4-methoxyphenyl group, a 3,5-dichloro-4-methoxyphenyl group, a 3,5-dichloro-4-octyloxyphenyl group, a 4-anilinophenyl group, a 4-acetoamidophenyl group, a 4-isopropylamidophenyl group, a 4-benzamidophenyl group, a 4-methylsulfonamidophenyl group, an octylsulfonamido group and a 2-(3-methyl-5-N,N-diethylaminopyridyl group.

The above-mentioned groups represented by X, Y or Z may also have a further substituent, if required.

When M represents a salt of Ni, Cu, Co, Zn, Fe, Pd or Pt, the examples thereof include an acetate, perchlorate, halide, fluoroborate or fluorophosphate each of the above.

Among the metal complex compounds of the invention, those having the following structure are preferred from the viewpoints of the absorption-reflection characteristics, preservation stability and ease of forming a complex, as regards a dye.

In the foregoing formula I or II, it is preferable that both X and Y are substituents capable of bonding to M such as a hydroxyl group, a mercapto group, an acylamino group substituted by an electron attractive group, an alkylsulfonamido group, an arylsulfonamido group, an alkoxy group, an alkylthio group, an arylthio group, an alkylamino group, and an aryl group substituted with the above-given substituent capable of bonding to M, and a heterocyclic group.

Further, a metal complex compound represented by the foregoing formula I is preferable to those represented by formula II. In the foregoing formula I or II, it is preferable when X represents a heterocyclic group and Y represents the foregoing substituent capable of bonding to M.

In formula I, it is particularly preferable when X represents a heterocyclic group and Y represents a phenyl group having a hydroxyl group, an acylamino group substituted by an electron withdrawing group, an alkylsulfonamido group or an arylsulfonamido group.

It is preferable when X represents a pyrazolyl group and Y represents a phenyl group having a hydroxyl group, an alkylsulfonamido group or an arylsulfonamido group. It is further preferable when X represents a pyrazolyl group and Y represents an alkylsulfonamido group or an arylsulfonamido group substituted phenyl group.

Z preferably represents an alkyl-substituted amino group, a hydroxyl group and a substituted or unsubstituted phenyl group having an alkyl group at the para-position. Z preferably represents a substituted or unsubstituted phenyl group having an alkyl substituted amino group at the para-position.

M preferably represents $Ni^{2+}$, $Cu^{2+}$ and any one of the salts thereof. Among them, $Ni^{2+}$ and any one of the salts thereof are preferable and, $Ni^{2+}$ is particularly preferable.

Among the compounds represented by the above Formula I or II, ones represented by the following Formula III are most preferable:

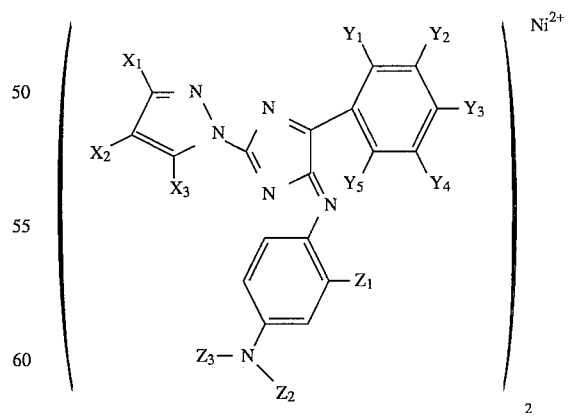

(III)

wherein $X_1$, $X_2$ and $X_3$ are each independently a hydrogen atom, an alkyl group or a halogen atom; $Y_1$ is an anionized alkylsulfonamido group or an anionized arylsulfonamido group; $Y_2$, $Y_3$, $Y^4$ and $Y_5$ are each independently a hydrogen atom, a halogen atom, an acylamino group, an alkylamino group or an alkoxyl group; $Z_1$ is an alkyl group or a hydrogen atom; and $Z_2$ and $Z_3$ are each independently an alkyl group.

A metal complex compound of the invention has an advantage that a light-absorption thereof per molecular weight is substantially high. Therefore, the molecular weight thereof is preferably not more than 1800 and optimally not more than 1300.

A metal complex compound of the invention may be prepared by bonding two dye molecules to one divalent metal. The details of the above-mentioned bonding have not yet been determined. However, it may be considered of formula I that a 4- or 6-dentate metal chelate is formed by bonding a metal atom to a dye molecule, that is, by 2 to 4 bondings made between M and a substituent represented by X or Y and, further, by two coordinated bondings made by lone paired electrons of an N atom of the principal ring.

It may be considered of formula II that a four-dentate metal chelate is formed by bonding a metal atom to a dye molecule, that is, by 4 bondings made between M and a substituent represented by X and Y.

Now, the following concrete examples of an metal complex compound of the invention will be given.

(1)

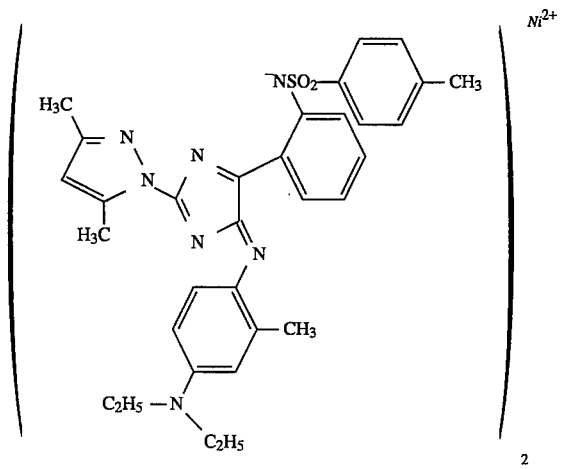

(2)

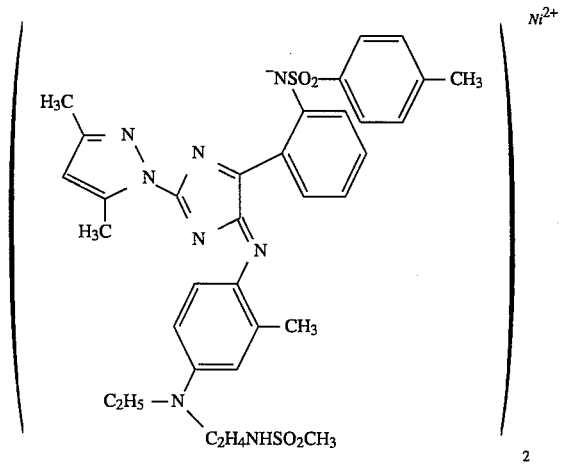

-continued
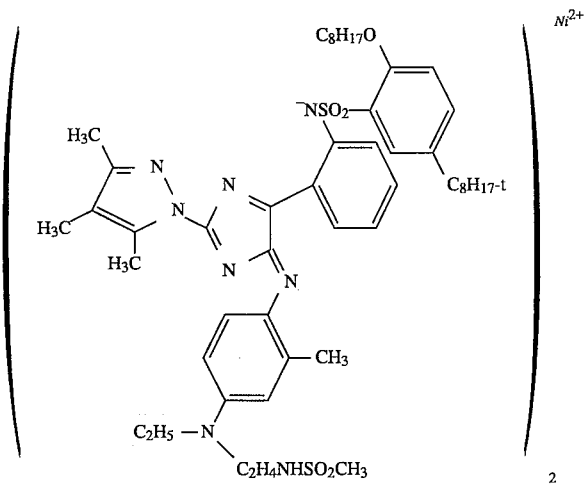
(3)
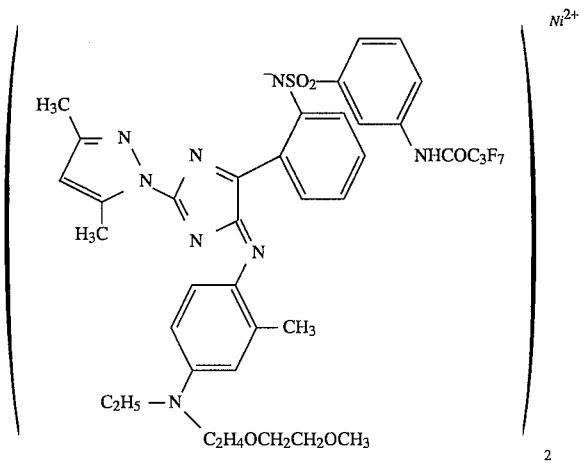
(4)
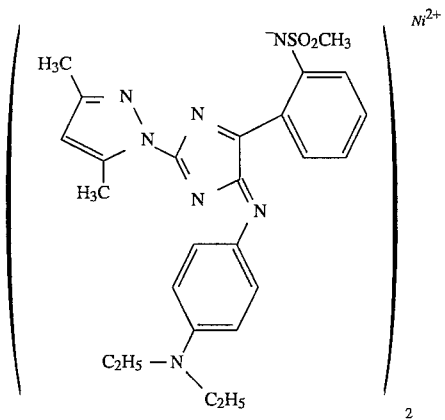
(5)

-continued
(6)
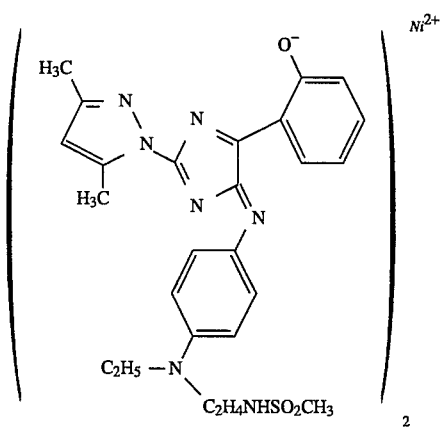
(7)
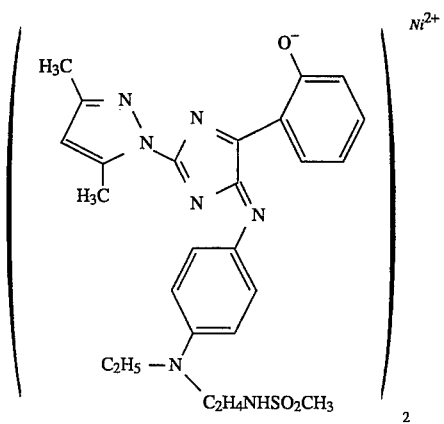
(8)
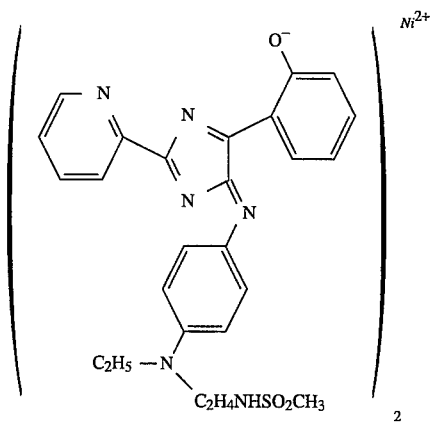

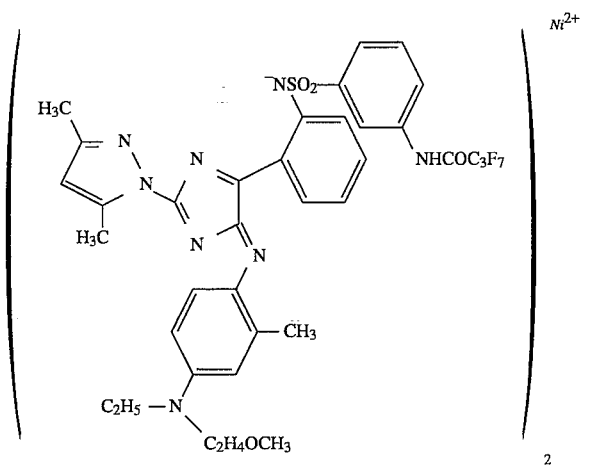
(9)
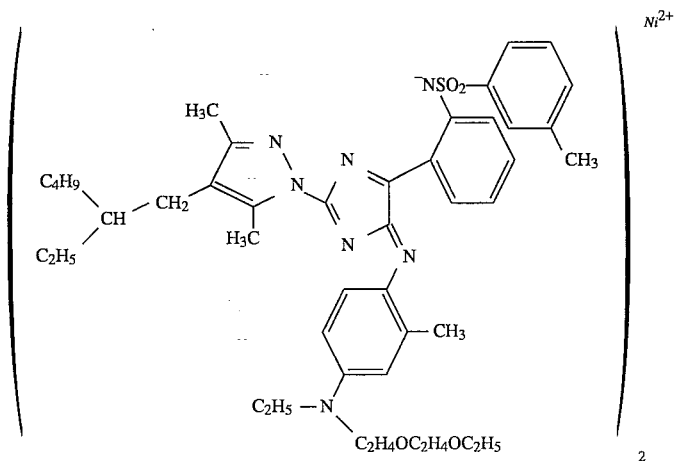
(10)
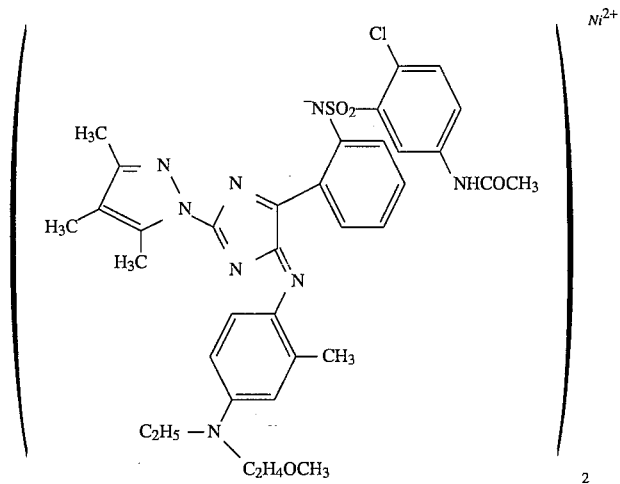
(11)

(12)
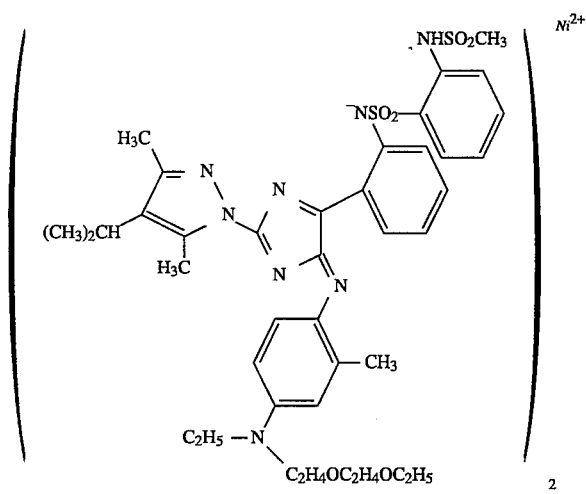
(13)
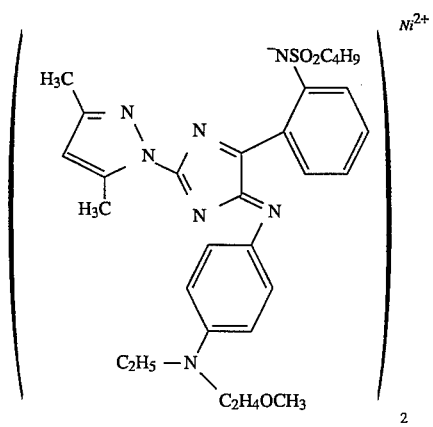
(14)
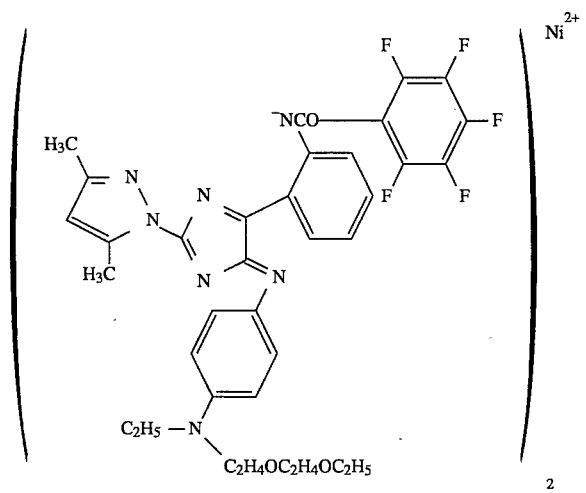

(15)
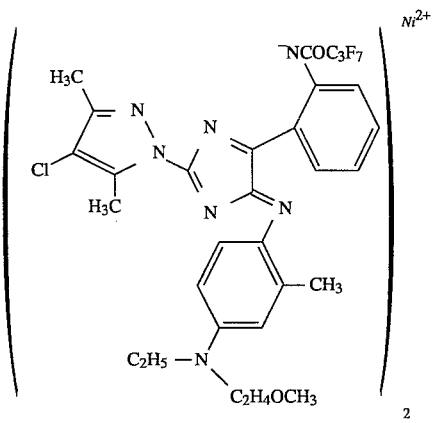
(16)
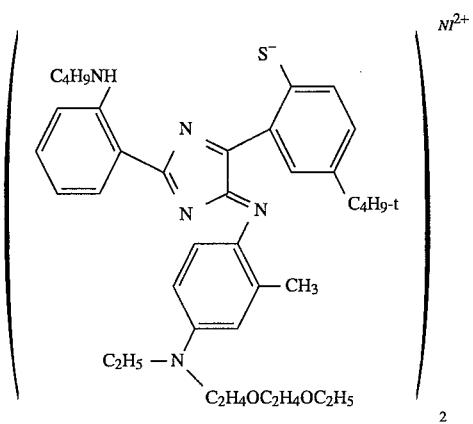
(17)
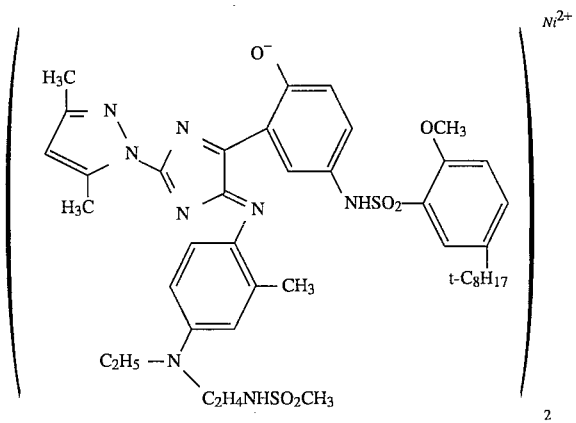

-continued
(18)
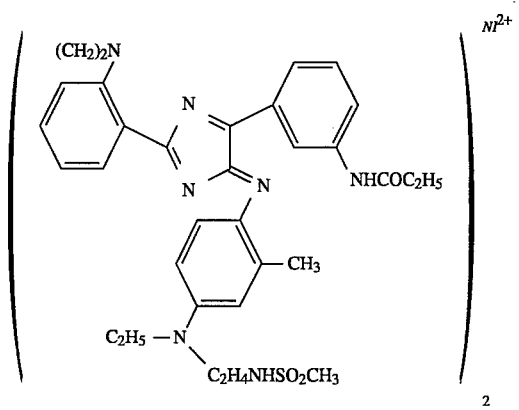
(19)
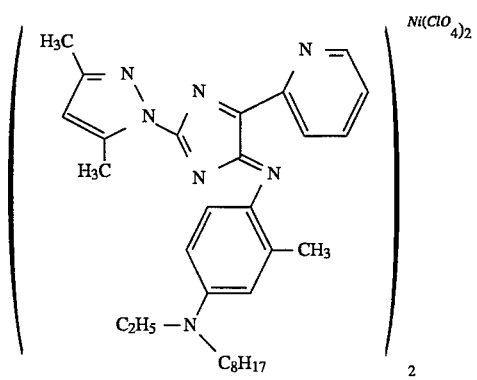
(20)
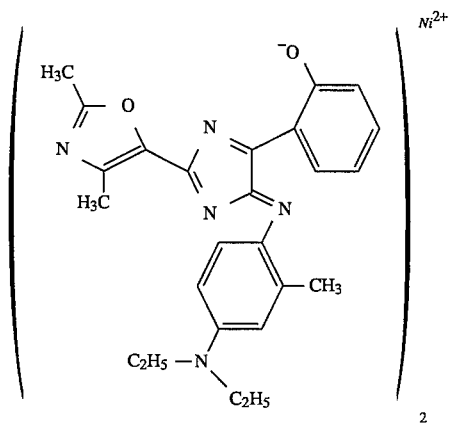

-continued
(21)
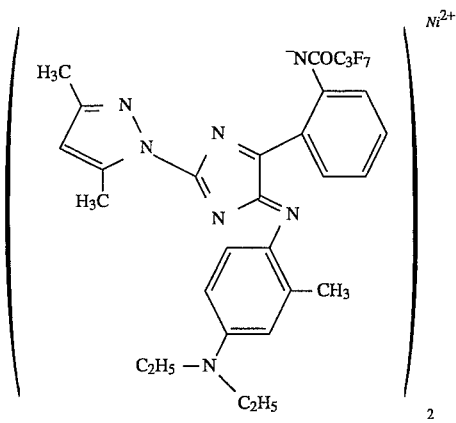
(22)
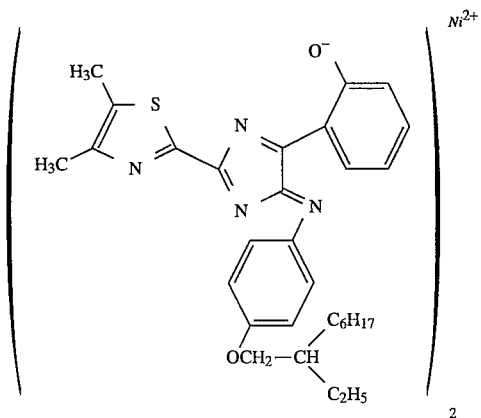
(23)
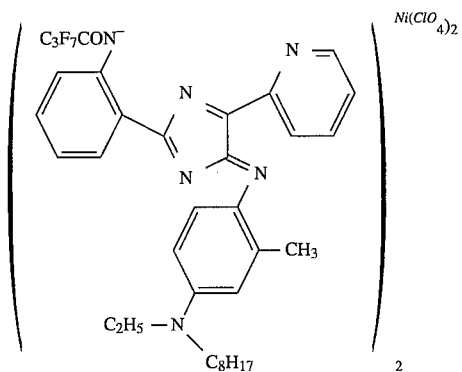

-continued
(24)
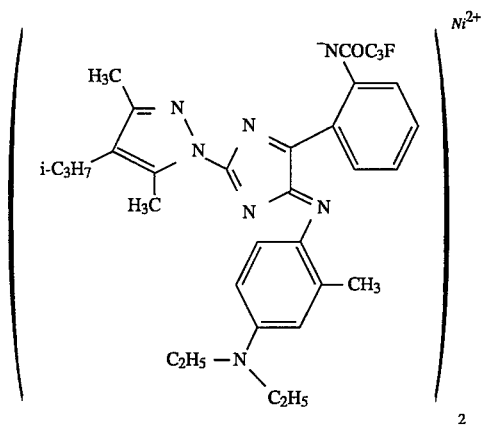
(25)
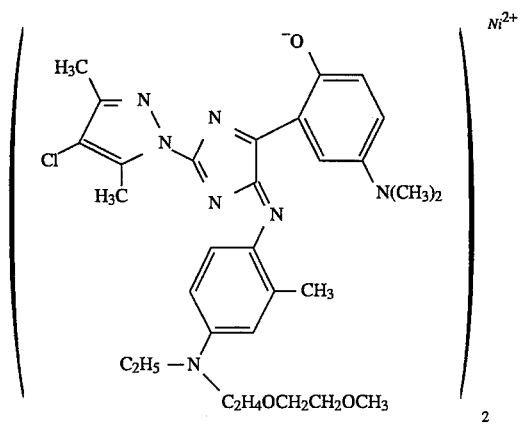
(26)
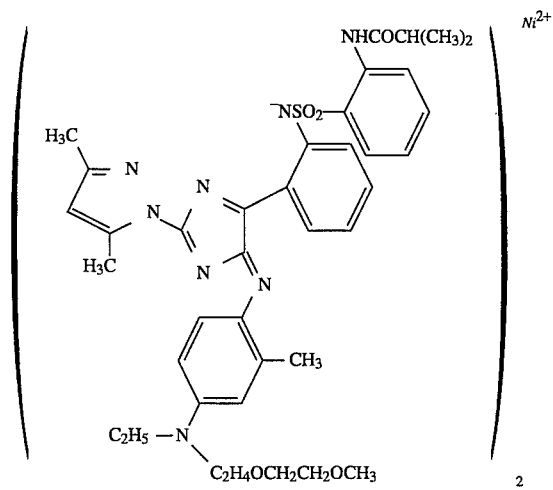

(27)
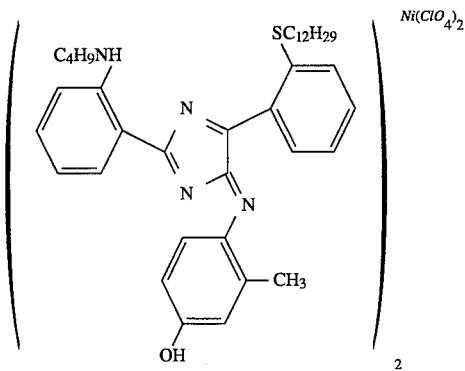
(28)
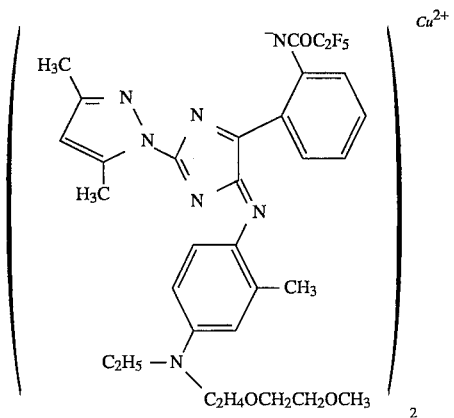
(29)
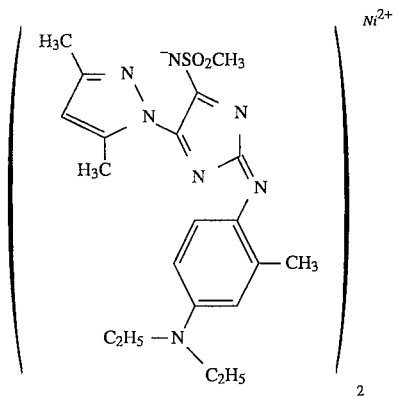

-continued
(30)
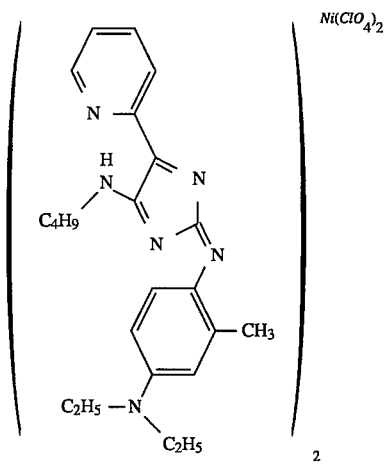
(31)
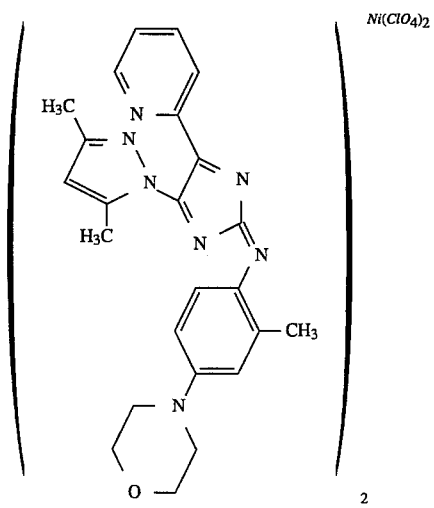

(32)
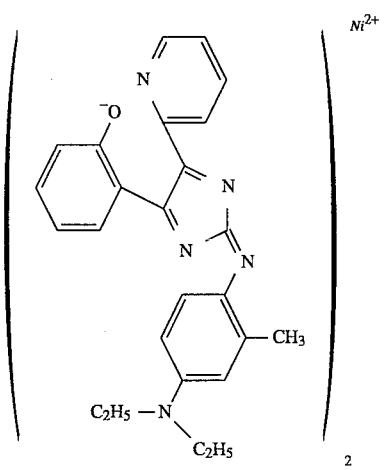
(33)
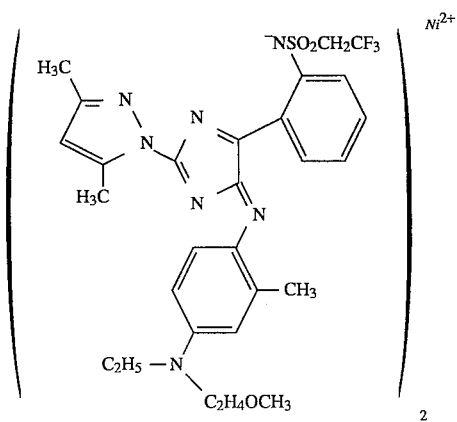
(34)
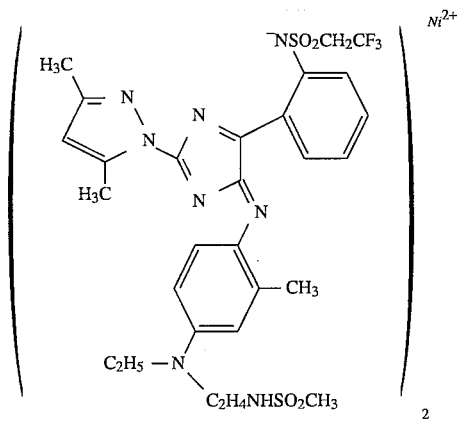

-continued (35)

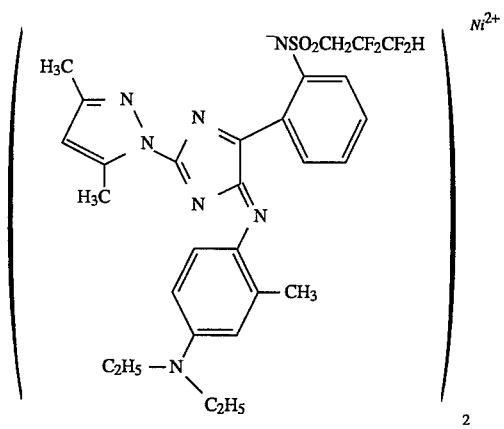

(36)

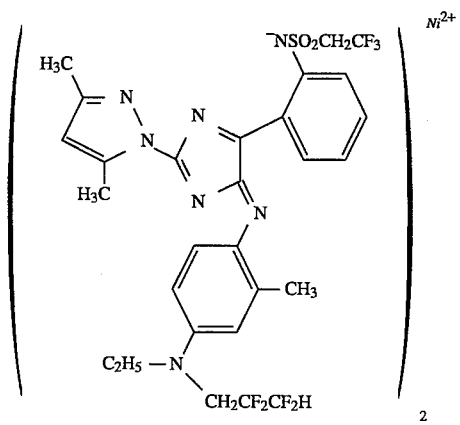

A metal complex compound of the invention can be prepared in the following manner; an imidazole derivative is so synthesized as to introduce a substituent capable of bonding to M, with reference to Beilstein, vol. 23, 24 & 25 and Berichte, vol. 34, p. 639, ibid., vol. 29, p. 2103 & ibid., vol. 92, p. 550, for example; then, an azomethine dye is prepared through an oxidization coupling reaction with a para-aminophenol or with a para-phenylenediamine derivative; further, the resulting azomethine dye is dissolved in a suitable solvent; and finally, a metal salt including, such as Ni acetate, Ni chloride, Cu chloride and Ni acetyl acetone is added to the resulting solution.

Now, the sythesis of a metal complex compound of the invention will be exemplified below.

SYNTHETIC EXAMPLE 1

Synthesis of Exemplified Compound (2)

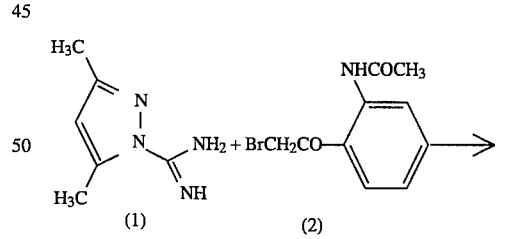

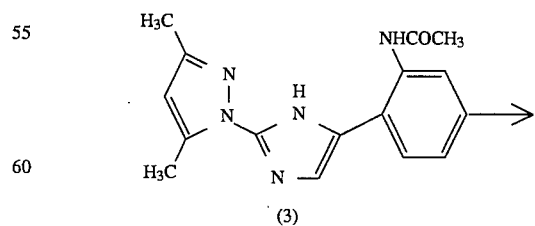

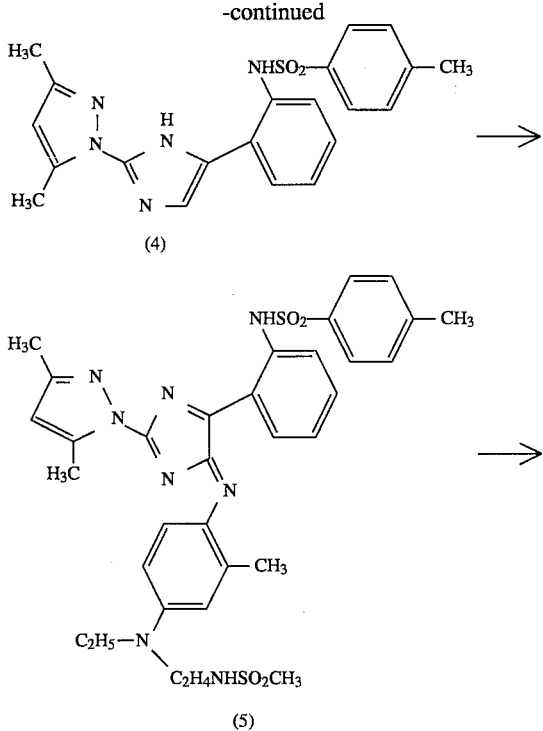

(4)

(5)

Exemplified compound (2)

The raw materials, 59 g of amidine (1) and 50 g of a bromoacetophenone derivative (2), were dissolved in 250 ml of chloroform, and the resulting solution was then refluxed for 2 hours. After it was washed and dried, the remaining solvent was distilled off and a recrystallization was then carried out of ethanol, so that 28 g of an objective intermediate (3) was prepared. Through an NMR, MASS spectrometry, the resulting intermediate was proved to be an objective. Next, 25 g of intermediate (3) and 50 ml of concentrated hydrochloric acid were each added to 300 ml of ethanol, and the resulting solution was then refluxed for one hour. After the remaining solvent was distilled off under reduced pressure, a neutralization was carried out by making use of an aqueous 20% potassium carbonate solution. After the resulting deposited crystals were filtrated and were then washed and dried, the crystals were dissolved in 100 ml of pyridine, and then 13 g of p-toluenesulfonyl chloride was added thereto. The resulting solution was stirred at room temperature for one hour. After confirming that the raw material amine was vanished, the resulting solution was neutralized by making use of hydrochloric acid, and was then extracted by making use of ethyl acetate, and dried. The resulting dried matter was refined through a column chromatography, so that 15 g of intermediate (4) was prepared. The resulting intermediate (4) was confirmed to be an objective, in an NMR, MASS spectrometry. Ten (10) grams each of intermediate (4) and 4-(N-ethyl-N-methyl-sulfonamidoethyl)- 2-methyl aniline were dissolved in 200 ml of ethyl acetate. To the resulting solution, a solution composed of 20 g of potassium carbonate and 100 ml of water was added, and then 50 ml of an aqueous solution of 20 g of ammonium persulfate was dropped in. After making a reaction for one hour and the resulting aqueous layer was then separated, the remaining solvent was distilled off. The resulting matter was refined in a column chromatography, so that 6 g of objective dye (5) could be prepared. The resulting dye (5) was proved to be an objective, by an NMR, MASS spectrometry. Dye (5) of 2 g was dissolved in 30 ml of methanol and, thereto, 0.6 g of Ni acetate tetrahydrate was added. After distilling off the remaining solvent, a recrystallization was carried out of methanol, so that 1.8 g of exemplified compound (2) of an objective metal complex compound could be prepared. It was proved to be an objective, by an IR and an elementary analysis.

SYNTHETIC EXAMPLE 2

Synthesis of Exemplified Compound (6)

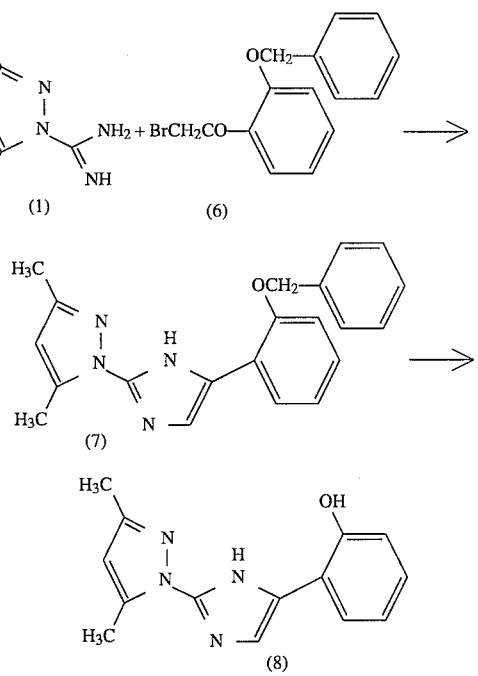

-continued

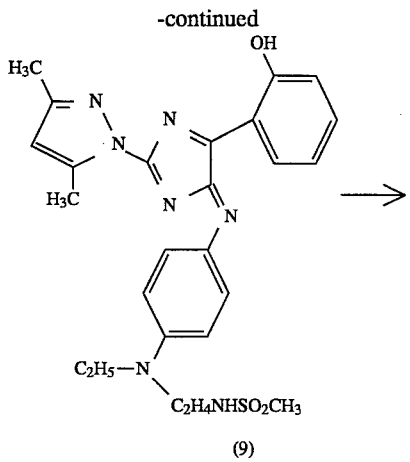

(9)

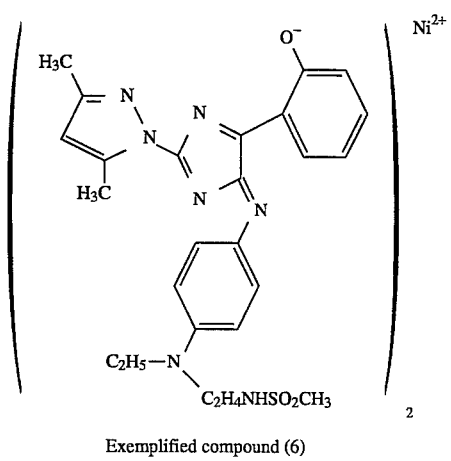

Exemplified compound (6)

The raw materials, 30 g of amidine (1) and 30 g of a bromoacetophenone derivative (6), were dissolved in 250 ml of chloroform and the resulting solution was then refluxed for 2 hours. After it was washed and dried, the remaining solvent was distilled off and a refinement was carried out in column chromatography, so that 18 g of an objective intermediate (7) could be prepared. In an NMR and a MASS spectrometry, the resulting intermediate (7) was proved to be an objective. Next, 10 g of intermediate (7) was dissolved in 100 ml of ethanol, and one gram of Pd/C was added thereto. Then, a catalytic hydrogenation was carried out under atmospheric pressure. After confirming that a theoretical amount of hydrogen was absorbed, a filtration was made and the remaining solvent was distilled off under reduced pressure. Then, a recrystallization was carried out of an ethyl acetate-hexane-mixed solvent, so that 8 g of intermediate (8) could be prepared. The resulting intermediate (8) was confirmed to be an objective by an NMR and a MASS spectrometry. Next, 8 g of intermediate (8) and 13 g of 4-(N-ethyl-N-methyl-sulfonamidoethyl)- 2-methyl aniline were dissolved in 200 ml of ethyl acetate. Thereto, a solution, containing 20 g of potassium carbonate added to 100 ml of water, was added, and 50 ml of an aqueous solution containing 20 g of ammonium persulfate was then dropped in. After making a reaction for one hour, and then the resulting aqueous layer was separated and the remaining solvent was distilled off, a recrystallization was carried out of ethyl acetate, so that 5 g of objective dye (9) was prepared. The resulting dye (9) was confirmed to be an objective by an NMR and a MASS spectrometry. Dye (9) of 2 g was dissolved in 30 ml of methanol, and 0.6 g of Ni acetate tetrahydrate was then added thereto. After distilling off the remaining solvent, a recrystallization was carried out of methanol, so that 1.2 g of exemplified compound (6) of an objective metal complex could be prepared. The resulting exemplified compound (6) was proved to be an abjective, by an IR and an elementary analysis.

A metal complex compound of the invention can be macromolecular by introducing a polymerizable substituent, if required, and, besides, it may also be processed into various forms such as an LB (Langmuir-Blodgett) layer formation made by introducing an oil-soluble or hydrophilic group, a dispersion made by an oil, and a microcapsulation.

A compound of the invention can be used independently or in combination with other dyes so as to be applicable to various purposes such as an optical recording medium, a dyestuff for a textile, a colorant for a resin paint or a printing ink, an image-forming material for a color copying machine, a color printer and a thermal recording material, and a filter-dye for a solid-state image-pickup tube or a color liquid-crystal display.

A metal complex compound of the invention may also be further improved in preservability by adding a variety of preservability-improving materials including, for example, a UV absorbent such as a benztriazolylphenol derivative, an antioxidant such as β-carotene, a tocopherol derivative, a hydroquinone derivative, a spiroindane derivative, a phenol derivative, an amine derivative, a thioether derivative, a Ni dithiol derivative, a Ni phenanthroline derivative and a Ni benzylidene aniline derivative, and a photostabilizer. They may also be added independently or in combination.

Now, an optical recording medium applied with a metal complex compound of the invention will be detailed below.

A substrate constituting an optical recording medium of the invention is required to be substantially transparent (in a transmittance of not less than 80%) in a laser wavelength region within the range of 700 to 900 nm that is used for the recording and replaying purposes. The configuration of such a substratum as mentioned above is to be about 1.2 mm in thickness and about 80 to 120 mm in diameter in the case of making use as an ordinary compact disc.

The materials for constituting a substrate include, for example, a transparent resin such as a polymethyl methacrylate resin, an acrylic resin, a polycarbonate resin, an epoxy resin, a polysulfone resin and a methylpentene polymer, and a glass plate.

On the outer surface, inner surface and inner.outer circumferential surfaces of a substratum, an oxygen-shielding coated layer may also be formed, if required.

On a substrate forming a recording layer thereon, it is preferable to form a tracking groove.

With a recording layer applied with a metal complex compound of the invention, the extinction coefficient κ in a laser-beam wavelength region can become preferable to serve as a recording layer for an optical recording medium and can have both of a light absorptivity suitable for making a recording operation and a reflectivity suitable for making a replaying operation. When an extinction coefficient κ in a laser-beam wavelength region is too large, a reflectivity may be lowered, so that any replaying operated by reflection light cannot satisfactorily be performed. When an extinction coefficient κ is too small, it may be hard to perform any recording operated by an ordinary recording power. A preferable extinction coefficient κ is within the range of 0.01 to 0.1.

On the other hand, in a laser-beam wavelength region, a refractive index n, or the substantial portion of a double refractive index, of a recording layer is preferable to be within the range of 1.8 to 4.0.

In a recording layer constituting an optical recording medium of the invention, any other kinds of dye compounds, various kinds of resins, surfactants, antistatic agents, dispersants, antioxidant, cross-coupling agents and so forth may be contained. Such a recording layer as mentioned above may also be formed on either one surface of a substrate or both surfaces thereof.

A preferable thickness of a recording layer is usually within the range of 500 Å to 3000 Å. There is no special limitation to the methods of forming a recording layer on a substrate. For example, the following various methods may be applied; namely, a spin-coating method, a dip-coating method, a spray-coating method, a blade-coating method, a roller-coating method, a bead-coating method, a wire-coating method and a curtain-coating method.

The solvents applicable to form a recording layer include, for example, a ketone type solvent such as cyclohexanone, an ester type solvent such as butyl acetate, an ether type solvent such as ethyl cellosolve, an alcoholic type solvent, an aromatic solvent such as toluene and a halogenated alkyl type solvent. Besides, a reflective layer may also be formed on a recording layer.

A reflective layer can be formed by making use of a metal having a high reflectivity, such as Au, Al-Mg alloy, Ag-Cu alloy, Al-Ni alloy, Ag, Pt and Cu, and in such a means as a vacuum evaporation or spattering operation. A thickness of a reflective layer is preferable to be not thinner than 500 Å.

On a reflective layer, a protective layer comprising, for example, a UV-setting resin may also be formed.

A thickness of a protective layer may be of the order within the range of 0.1 to 100 μm; and the hardness thereof is preferable within the range of H to 8H at 25° C. in terms of a pencil hardness.

Between a recording layer and a reflective layer, an adhesion layer may also be interposed so as to bring them into close contact with each other. A thickness of an adhesion layer is to be preferably within the range of 10 to 300 Å.

As for a light source for recording and/or replaying an optical recording medium of the invention, it may be considered to make use of a solid state laser, a gas laser, a dye laser and a semi-conductor laser. As is seen in a compact disc, a semi-conductor laser is preferable from the viewpoints of the inexpensiveness, compactness and low power consumption. From the fact that a compound of the invention has a particularly high recording sensitivity, a semi-conductor laser is preferable to have a wavelength region within the range of 650 to 830 nm and, more preferably 770 to 830 nm.

EXAMPLES

Example 1

Now, the spectral absorption characteristics of a metal complex compound of the invention will be shown below.

Spectral Absorption Characteristics

Table 1 shows the spectral absorption characteristics of both of a metal complex compound of the invention and the following comparative compounds thereto; provided that the latter shows the spectral absorption characteristics of an imidazole type azomethine dye without forming any metal complex, that was contained in a methanol phase, as the latter compound.

TABLE 1

|  | Absorption maximum | ε max |
| --- | --- | --- |
| Exemplified compound (1) | 679 nm | 157507 |
| Exemplified compound (2) | 677 nm | 123566 |
| Exemplified compound (3) | 675 nm | 116269 |
| Exemplified compound (4) | 694 nm | 86155 |
| Comparative compound (A) | 694 nm | 38500 |

Comparative compound (A)

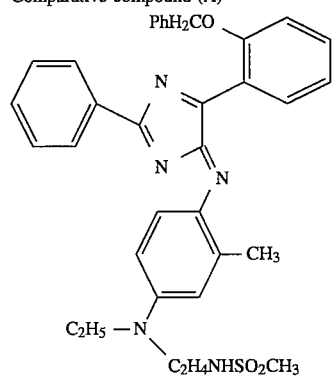

As is obvious from the contents of Table 1, it was proved that every one of the exemplified compounds of the invention was a dye having an absorption maximum in a preferable wavelength region and an excellently high ε, as a cyan dye, in comparison with the comparative compounds.

Example 2

Now, the following examples of an optical recording medium applied with a metal complex compound of the invention will be given below.

Evaluation on an Optical Recording Medium

Each of the evaluation was made, in the following procedures, on the absorption maximum, light resistance, optical recording characteristics and so forth of a thin layer.

(1) Formation of a recording layer

One gram each of exemplified inventive compounds (1), (2), (3) and (6) and comparative compounds (B) and (C) were weighed, and they were dissolved in 50 ml of cyclohexanone, respectively. The coating solutions were coated on glass-made substrata (each having a thickness of 1.1 mm and a diameter of 80 mm) in a spin-coating method and were then dried at 80° C. for 30 minutes, so that the recording layers each having a thickness of about 1000 were formed on the glass-made substrata, respectively.

(2) Light stability test

By making use of a xenon fade-o-meter (manufactured by Suga Testing Instrument Co.), each recording layer sample was exposed to xenon rays, and then the ratios of residual dyes were measured after exposing the samples thereof to xenon rays.

For the exposure conditions, the illumination intensity on the surface of a recording layer was set to be 70,000 lux, the temperature was set to be 43° C. when exposing the samples to xenon rays, and the exposure time was set to be 30 hours. A dye residual ratio was obtained by measuring the light transmittance of a dye in the maximum absorption wavelength region before and after exposing the dye to xenon rays and then by the following formula.

Dye residual ratio=[(100−T)/(100−T₀)]×100 wherein $T_0$ represents a transmittance obtained before exposing a sample to xenon rays, and T represents a transmittance obtained after exposing a sample to xenon rays. The results thereof will be shown in Table 2.

TABLE 2

| Sample No. | Compound | Absorption maximum (nm) | Dye residual ratio (%) |
|---|---|---|---|
| 1 | Exemplified compound (1) | 699 | 97 |
| 2 | Exemplified compound (2) | 698 | 98 |
| 3 | Exemplified compound (3) | 682 | 94 |
| 4 | Exemplified compound (6) | 749 | 100 |
| 5 | Comparative compound (B) | 702 | 63 |
| 6 | Comparative compound (C) | 832 | 92 |

Comparative compound (B)

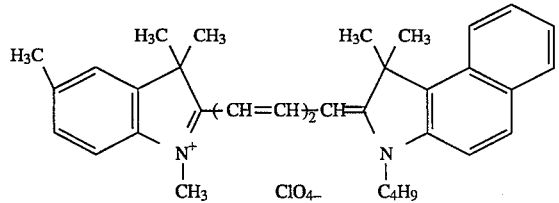

Comparative compound (C)

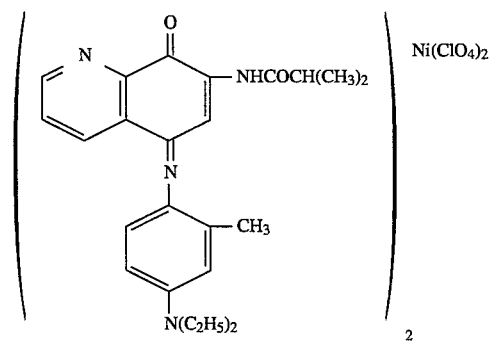

As is obvious from the contents of Table 2, it was proved to be as follows. Samples No. 1 through No. 4, which were each a recording medium applied with a metal complex compound of the invention, have had the absorption maximum equivalent to that of comparative sample 5 applied with cyanine dye, a dye residual ratio higher than that of the comparative samples and a light stability more excellent than that of the comparative samples.

On the other hand, sample 6 applied with another metal complex compound different from those of the invention was proved to have a too long wavelength in the absorption maximum thereof, so that the sample 6 was not suitable for an optical recording medium.

Example 3

On a 5 inch-diameter polycarbonate substrate with a groove, a recording layer was coated by making use of metal complex compound 36 of the invention. Thereon, a gold 1000 Å-thick reflective layer and a 5 μm-thick UV-curing resin protective layer were formed in this order in an ordinary manner to prepare optical recording medium 7 of the invention. Further, a comparative optical recording medium 8 was prepared in the same manner as in recording medium 7 except that the metal complex was replaced by comparative comple B. Both of the samples each had a reflectivity of more than 70%. Information was recorded on the samples with various recording power by light of 780 nm emitted from a semiconductor laser. The information recorded on the sample was readout repeatedly by laser beam with 0.8 mW. The minimum power necessary to record the information (Min. power) and the repeating times of reading-out until reading error was occurred (Rep. time) were determined. On the other hand, the other specimens of the samples were subjected to the same test after uniformly exposure to light of 70,000 lux for 30 hours by xenon Fade-o-Meter used in Example 2. Thus obtained test resuls are shown in Table 3.

TABLE 3

| Sampl No. | Without uniform exposure | | After exposure by xenon Fade-o-Meter | |
|---|---|---|---|---|
|  | Min. Power | Rep. times | Min. Power | Rep. times |
| 7 (Inv) | 7 mW | >10⁶ | 7 mW | >10⁶ |
| 8 (Comp) | 7 mW | <10⁴ | — | — |

After exposure by xenon Fade-o-Meter, information cannot be recorded on the comparative sample 8.

As is shown in Table 3, it is proved that the inventive sample 7 satisfied the CD standard of recording and reading characteristics and that the inventive recording medium was excellent in the light stability and has stable recording and reading-out properties. Contrary to this, in the comparative recording medium, Sample 8, the readout error occurred which was caused by lowering in the refrectivity by repeated irradiation by the laser beam for reading-out the information. Furthermore, any information could not be recorded on the comparative recording medium after exposure by the xenon Fade-o-Meter.

What is claimed is:

1. A metal complex compound represented by the following Formula I or II

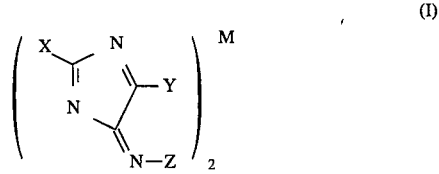

(I)

-continued

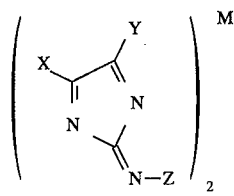

wherein at least one of X and Y is substituted aryl having a substituent independently selected from hydroxyl, mercapto, acylamino, having an electron withdrawing group as a substituent, alkylsulfonamido, arylsulfonamido, alkoxy, alkylthio, and alkylamino; when one of X and Y is said substituted aryl, another of X and Y is heterocyclic, which may have an alkyl group or a halogen atom as a substituent, hydrogen, or a group of non-metal atoms; Z is substituted aryl having a substituent selected from hydroxyl, amino, alkyl substituted amino, alkoxy, anilino, acylamino, add alkylsulfonamido, at the para-position thereof; and M is $Ni^{2+}$ ion or its salt, $Cu^{2+}$ ion or its salt, $Co^{2+}$ ion or its salt, $Zn^{2+}$ ion or its salt, $Fe^{2+}$ ion or its salt, $Pd^{2+}$ ion or its salt, or $Pt^{2+}$ ion or its salt.

2. The compound of claim 1, wherein said compound is a compound represented by Formula III;

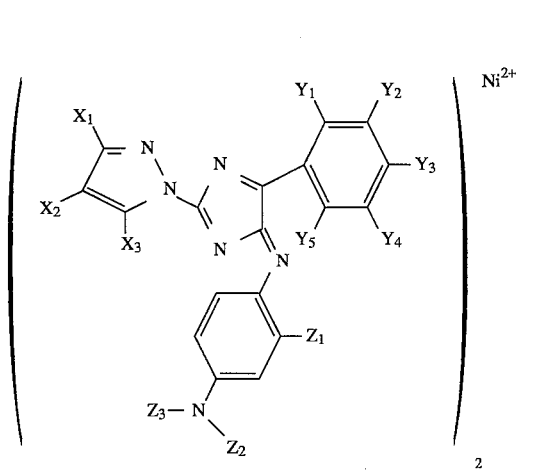

wherein $X_1$, $X_2$ and $X_3$ are each independently a hydrogen atom, an alkyl group or a halogen atom; $Y_1$ is an anionized alkylsulfonamido group or an anionized arylsulfonamido group; $Y_2$, $Y_3$, $Y^4$ and $Y_5$ are each independently a hydrogen atom, a halogen atom, an acylamino group, an alkylamino group or an alkoxyl group; $Z_1$ is an alkyl group or a hydrogen atom; and $Z_2$ and $Z_3$ are each independently an alkyl group.

3. The compound of claim 1, wherein said electron withdrawing group is a group having a positive Hammett's σ value.

4. The compound of claim 3, wherein said electron withdrawing group is a halogen atom, a cyano group, a nitro group or an alkylsulfonamido group.

5. The compound of claim 1, wherein both of X and Y are each a hydroxyl group, a mercapto group, an acyl group having an electron withdrawing group as a substituent, an alkylsulfonamido group, an arylsulfonamido group, an alkoxyl group, an alkylthio group, an arylthio group, an alkylamino group, an aryl group having a substituent selected from a hydroxyl group, a mercapto group, an acyl group having an electron withdrawing group as a substituent, an alkylsulfonamido group, an arylsulfonamido group, an alkoxyl group, an alkylthio group, an arylthio group and an alkylamino group, or a heterocyclic group.

6. The compound of claim 5, wherein both of X and Y are each an aryl group having a substituent selected from a hydroxyl group, a mercapto group, an acyl group having an electron withdrawing group as a substituent, an alkylsulfonamido group, an arylsulfonamido group, an alkoxyl group, an alkylthio group, an arylthio group and an alkylamino group, or a heterocyclic group.

7. The compound of claim 5, wherein X is a heterocyclic group and Y is an aryl group having a substituent selected from a hydroxyl group, a mercapto group, an acyl group having an electron withdrawing group as a substituent, an alkylsulfonamido group, an arylsulfonamido group, an alkylthio group, an arylthio group and an alkylamino group, or a heterocyclic group.

8. The compound of claim 7, wherein said compound is a compound represented by formula I in which X is a heterocyclic group and Y is a phenyl group having a substituent selected from a hydroxyl group, an acylamino group having an electron withdrawing group as a substituent, an alkylsulfonamido group and an arylsulfonamido group.

9. The compound of claim 1, wherein Z is a phenyl group having an alkylamino group, a hydroxyl group or an alkoxyl group as a substituent at the para-position thereof.

10. The compound of claim 9, wherein Z is a phenyl group having an alkylamino group as a substituent at the para-position thereof.

11. The compound of claim 1, wherein M is $Ni^{2+}$ ion or its salt, or $Cu^{2+}$ or its salt.

12. The compound of claim 11, wherein M is $Ni^{2+}$ or its salt.

13. The compound of claim 1, wherein said group of nonmetal atoms is cyano, hydroxyl, amino, alkyl, cycloalkyl, alkenyl, aralkyl, alkoxy, sulfonamido, anilino, mercapto, acylamino, ureido, alkoxycarbonyl, carbamoyl, sulfamoyl, sulfo, carboxyl, alkoxycarbonylamino, aryl, or heterocyclic.

14. The compound of claim 8 wherein said compound is a compound represented by Formula I in which X is a pyrazolyl group, which may have an alkyl group or a halogen atom as a substituent, and Y is a phenyl group having a substituent selected from a hydroxyl group, an alkylsulfonamido group and an arylsulfonamido group.

15. The compound of claim 8 wherein said compound is a compound represented by Formula I in which X is a pyrazolyl group, which may have an alkyl group or a halogen atom as a substituent, and Y is a phenyl group having an alkylsulfonamido group or an arylsulfonamido group as a substituent.

* * * * *